United States Patent [19]

Atherton et al.

[11] 3,957,729

[45] May 18, 1976

[54] PROCESS FOR THE PREPARATION OF TRIDECADIEN DERIVATIVES

[75] Inventors: Frank Ratcliffe Atherton, Welwyn Garden City Herts; Albert Pfiffner, Arlesheim, Switzerland

[73] Assignee: Hoffmann-La Roche Inc., Nutley, N.J.

[22] Filed: Dec. 5, 1968

[21] Appl. No.: 781,603

[30] Foreign Application Priority Data

Dec. 18, 1967 United Kingdom............... 57283/67

[52] U.S. Cl................... 260/348 A; 260/348 R; 260/404; 260/410.9 R; 260/413; 260/465.9; 260/961; 260/593 R; 260/632 R; 260/DIG. 44; 424/304; 424/312; 424/318; 424/278; 424/320; 424/DIG. 12

[51] Int. Cl.²............. C07D 303/42; C07C 102/00; C07C 67/00

[58] Field of Search.................. 260/410.9, 410.9 V, 260/348 A, 348.5 US, 404, 413 US, 465.9 US, 410.9 US

[56] References Cited

UNITED STATES PATENTS

| | | | |
|---|---|---|---|
| 3,157,660 | 11/1964 | Stilz et al............................ | 260/283 |
| 3,177,226 | 4/1965 | Stilz et al.......................... | 260/340.5 |
| 3,666,780 | 5/1972 | Calame et al....................... | 260/405 |
| 3,773,805 | 11/1973 | Siddall et al....................... | 260/404 |

OTHER PUBLICATIONS

Dahm et al., J. Am. Chem. Soc. 89, 20, 9/27/67 pp. 5292–5294 Chemical Abstracts 68 95597R, 5/20/68.

Noller, "Chemistry of Organic Compounds", W. B. Saunders Co., Philadelphia, (1965), pp. 536–537, relied on.

*Primary Examiner*—Alton D. Rollins
*Assistant Examiner*—Diana G. Rivers
*Attorney, Agent, or Firm*—Samuel L. Welt; Bernard S. Leon; William H. Epstein

[57] ABSTRACT

A process for preparing 2-cis,6-trans-10,11-epoxy-6-ethyl-3,11-dimethyl-2,6-tridecadien derivatives and mixtures of said 2-cis,6-trans-tridecadienn derivatives with its corresponding 2-trans,6-trans-geometric isomers which are useful in killing and preventing proliferation of insects, by upsetting their hormone balance including intermediates in this process.

5 Claims, No Drawings

PROCESS FOR THE PREPARATION OF TRIDECADIEN DERIVATIVES

SUMMARY OF THE INVENTION

This invention is directed to 2-cis,6-trans-10,11-epoxy2,6-tridecadien derivatives of the formula:

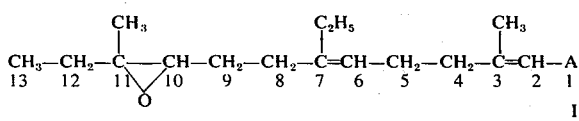

I wherein A is selected from the group consisting of cyano, carboxy, loweralkoxycarbonyl, aminocarbonyl and lower alkyl substituted aminocarbonyl and mixtures of said 2-cis,6-trans-tridecadien derivatives with its corresponding 2-trans,6-trans geometric isomer. The aforementioned compounds of formula I above and said mixtures thereof upset the hormone balance of pests such as insects, to prevent them from growing and reproducing.

The aforementioned isomeric form of formula I above and said mixtures thereof are prepared by reacting a 5-transdodecen-2-one of the formula:

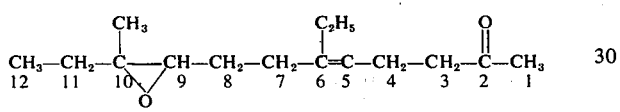

II with a phosphorane of the formula:

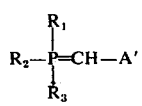

III wherein A' is selected from the group consisting of cyano, lower alkoxycarbonyl, aminocarbonyl or lower alkyl-substituted aminocarbonyl; and $R_1$, $R_2$ and $R_3$ are aryl or diloweralkylamino or with a phosphine oxide of the formula:

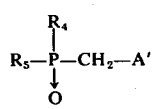

IV wherein A' is as above and $R_4$ and $R_5$ are selected from the group consisting of aryl, aryloxy and lower alkoxy to form a mixture of the 2-cis,6-trans-10,11-epoxy-2,6-tridecadien derivative of the formula:

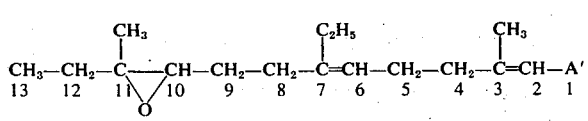

I-a wherein A' is as above
and the corresponding 2-trans,6-trans isomeric form.

Thereafter, if desired, separating the said 2-cis,6-trans isomeric forms from said mixture of formula I-a above. If desired, the 2-cis,6-trans isomeric form of the compound of formula I-a and said mixtures thereof wherein A' is a lower alkoxycarbonyl group can be saponifid to said 2-cis,6-trans isomeric form of formula I and said mixtures thereof wherein A is carboxyl.

Alternatively, the aforementioned 2-cis,6-trans isomeric form of formula I-a above as well as said mixtures thereof can be prepared by reacting a 5-trans-9-dodecadien-2-one of the formula:

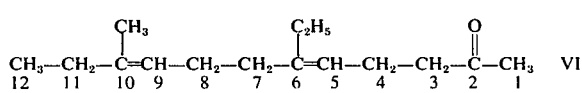

VI with the phosphorane of the formula III above or the phosphine oxide of formula IV above to produce a mixture of the 2-cis,6-trans2,6,10-tridecatrien of the formula:

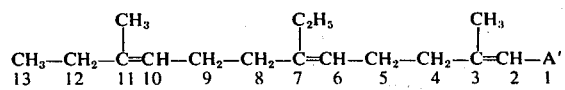

VII wherein A' is as above
and the corresponding 2-trans,6-trans isomeric form. If desired, the 2-cis,6-trans isomer can be separated from said isomeric mixture of formula VII. The 2-cis,6-trans isomer or said mixture of formula VII is then epoxidized to produce the 2-cis,6-trans isomeric form of formula I-a and the mixture thereof with the corresponding 2-trans,6-trans isomeric form.

In accordance with a preferred embodiment of this invention, it has been found that when a phosphine oxide of the formula:

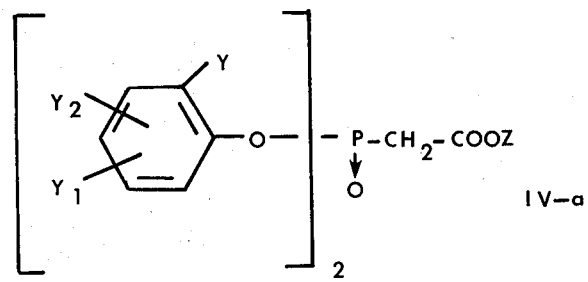

IV-a wherein Z is lower alkyl; Y is hydrogen or an electron donating group and $Y_1$ and $Y_2$ are selected from the group consisting of hydrogen, halogen, lower alkoxy and nitro is reacted with the 5-trans isomeric form of formulae II or VI above, the formation of the 2-cis,6-trans isomer form is preferred in the aforementioned mixtures of formulae I-a and VII obtained by the reaction. In some cases, by utilizing the reactant of formula IV-a above mixtures containing about 50 percent of the 2-cis, 6-trans isomeric form are produced.

DETAILED DESCRIPTION OF THE INVENTION

The numbering of the trideca chain of formulae I, I-a and VII above and the dodecen-2-one chain in formulae II and VI above is shown for the purposes of convenience.

As used throughout the application, the term "lower alkyl" comprehends both straight and branched chain saturated hydrocarbon groups containing from 1 to 6 carbon atoms such as methyl, ethyl, propyl, isopropyl, etc. The term "lower alkoxy" comprehends lower alkoxy groups containing from 1 to 6 carbon atoms such as methoxy, propoxy, ethoxy, etc. The term "lower alkoxy carbonyl" as used throughout this application, comprehends lower alkoxy carbonyl groups wherein the lower alkoxy substituent contains from 1 to 6 carbon atoms. Examples of lower alkoxy carbonyl groups are methoxy-carbonyl, ethoxy-carbonyl and isopropoxy-carbonyl with the methoxy-carbonyl and ethoxy-carbonyl groups being preferred.

The term "lower alkyl-substituted aminocarbonyl" groups as used throughout this application comprehends both monolower alkyl substituted amino carbonyl groups and dilower alkyl substituted alkyl aminocarbonyl groups wherein the lower alkyl moiety or moieties contain from 1 to 6 carbon atoms. Among the preferred lower alkyl substituted amino alkyl groups are monomethylamino-carbonyl, dimethylamino-carbonyl, monoethylaminocarbonyl, diethylamino-carbonyl, monoisopropylamino-carbonyl and diisopropylamino-carbonyl.

The term "dilower alkylamino" as used throughout the application includes dilower alkylamino groups wherein the lower alkyl moieties contain from 1 to 6 carbon atoms such as methyl, ethyl, isopropyl, etc. As used in this application, the term "halogen" includes all four halogens such as bromine, chlorine, fluorine and iodine.

The term "lower alkoxy" as used throughout the specification includes lower alkoxy groups containing from 1 to 6 carbon atoms such as ethoxy, isopropoxy, propoxy, methoxy, etc. The term "aryl" as used throughout the application includes mono-nuclear aryl groups such as phenyl which can be unsubstituted or substituted in one or more positions with a lower alkyl, halogen, an electron donating group, lower alkoxy, amino, nitro, mono- and di-substituted lower alkylamino, etc., or polynuclear aryl groups such as naphthyl, anthryl, phenanthryl, azulyl, etc. which may be unsubstituted or substituted with one or more of the aforementioned groups. The term "aryloxy" comprehends aryloxy groups wherein the aryl moiety is defined as above.

When the term "cis" is utilized in this application, it designates that the two largest substituents attached across the double bond or the epoxy bridge are on the same side of the double bond or epoxy bridge. The term "trans" as utilized in this application, designates that the largest substituents attached across the double bond or epoxy bridge are on opposite sides of the double bond or epoxy bridge.

Among the compounds of formula I which are effective in the control of pests, are the following:

racemic 10,11-epoxy-7-ethyl-3,11-dimethyl-10,11-cis-tridecadien-(2 cis, 6trans)-oic-(1) acid;

racemic 10,11-epoxy-7-ethyl-3,11-dimethyl-10,11-trans-tridecadien-(2 cis, 6 trans)-oic-(1) acid;

racemic 10,11-epoxy-7-ethyl-3,11-dimethyl-10,11-cis-tridecadien-(2 cis, 6 trans)-oic-(1) acid methyl- or ethyl- ester; and racemic 10,11-epoxy-7-ethyl-3,11-dimethyl-10,11-trans-tridecadien-(2 cis, 6 trans)-oic-(1) acid methyl or ethyl ester.

The 2 cis, 6 trans derivatives of formula I as well as said mixtures thereof are useful in the control of pests such as *Tenebrio molitor* (yellow mealworm), *Tineola biselliella* (clothes moth), *Carpocapsa pomonella* (codling moth), *Leptinotarsa decemlineata* (Colorado beetle), *Calandra granaria* (grain weevil), etc.; In contrast to most of the known pest-control agents which kill, disable or repell the pests by acting as contact-poisons and feed-poisons, the 2 cis, 6 trans derivatives of formula I above and said mixtures thereof prevent maturation and proliferation of these pests by upsetting their hormone balance. In insects, for example, the transformation into the imago is disturbed. Furthermore, the sequence of generations is interrupted and the insects are indirectly killed.

The 2 cis, 6 trans derivatives of formula I above and said mixtures thereof are practically non-toxic to vertebrates. The toxicity of these derivatives and said mixtures thereof is greater than 1000 mg/kg body weight. Moreover, these derivatives and said mixtures are readily degraded and the risk of accumulation is therefore excluded. Therefore, these derivatives and said mixtures can be used without fear of danger in the control of pests in animals, plants; foods; and textiles.

Generally for control of pests it is preferred to utilize the 2-cis, 6-trans-10,11-epoxy-7-ethyl-3,11-dimethyl-2,6-tridecadien derivatives of formula I above. However, mixtures of this compound with the 2-trans-6-trans-sterioisomer can also be utilized. It is generally preferred that this mixture contain at least 10% by weight of the 2-cis-6-trans-isomer and at most 90% by weight of the 2-trans-6-trans-isomer. Mixtures which contain above 95% by weight of the 2 cis, 6 trans-isomer of formula I and 5% by weight of the corresponding 2 trans, 6 transisomer are very effective in the control of pests.

Generally, in controlling invertebrate animals, the compounds of formula I above and said mixtures thereof are applied to the material to be protected, e.g., foodstuffs, feeds, textiles, plants in an amount of from about 0.01 percent to 0.1 percent by weight of the material to be protected. Generally, it is preferred to utilize the compounds of formula I above and said mixtures thereof in a composition with a suitable inert carrier. Any conventional inert carrier can be utilized.

The composition which contains an effective amount of the compounds of formula I above or said mixtures thereof should be applied to the material to be protected to provide a concentration of from about 0.01 percent to 0.1 percent of the compound of formula I above or said mixtures thereof on said material.

The 2-cis, 6-trans derivatives of formula I and said mixtures thereof can, for example, be used in the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them $_1$ by the action of external influences (e.g., contact with moisture) or in the animal body itself.

The 2-cis, 6-trans derivatives of formula I above and said mixtures thereof can be used as solutions suitable for spraying on the material to be protected which can be prepared by dissolving or dispersing these derivatives or said mixtures thereof in a solvent such as mineral oil fractions; cold tar oils; oils of vegetable or animal origins; hydrocarbons such as naphtalenes; ketones such as methyl ethyl ketone; or chlorinated hydrocarbons such as tetrachloroethylene, tetrachlorobenzene, and the like. The compounds of formula I above or said mixtures thereof can also be prepared in forms suitable for dilution with water to form aqueous liquids such as, for example, emulsion concentrates, pastes or powders. The compounds of formula I above or said mixtures thereof can be combined with solid carriers for making dusting or strewing powders as, for example, talc, kaolin, bentonite, calcium carbonate, calcium phosphate, etc. The compositions containing the 2-cis, 6-trans derivatives of formula I above or said mixtures thereof can contain, if desired, emulsifiers, dispersing agents, wetting agents, or other active substances such as fungicides, bacteriacides, nematocides, fertilizers and the like.

In accordance with this invention, the compounds of formula I-a can be prepared by reacting the formula II above with the phosphorane of the formula III above. This reaction is generally carried out in the presence of an organic acid catalyst in an inert organic solvent. Any conventional organic acid can be utilized as the catalyst in carrying out this invention. Generally it is preferred to utilize an organic acid such as acetic acid or benzoic acid. The organic acid is present in the reaction medium in catalytic quantities. In carrying out this reaction, any conventional inorganic solvent can be utilized. Among the conventional inert organic solvents which can be utilized in accordance with this invention are included benzene, toluene, N,N-dimethylformamide, 1,2-dimethoxyethane and dioxane. In carrying out this reaction, temperature and pressure are not critical, and this reaction can be carried out at room temperature and atmospheric pressure. However, elevated or reduced temperatures can be utilized. Generally, this reaction is carried out at a temperature of from about 15°C. to the boiling temperature of the solvent utilized.

The phosphoranes of formula III above are prepared by the known procedures from the corresponding phosphonium salts. In accordance with this invention, $R_1$, $R_2$ and $R_3$ can be aryl or dialkylamino group. The aryl groups which may form the substituent designated by $R_1$, $R_2$ and $R_3$ include mononuclear aryl groups such as phenyl or substituted phenyl such as tolyl, xylyl, mesityl, 4-methoxyphenyl, etc. The aryl substituent can be a polynuclear aryl group such as naphthyl, anthryl, phenanthryl, azulyl, etc. The dialkylamino groups which are designated by $R_1$, $R_2$ and $R_3$ are dilower alkyl amino groups preferably containing from 1 to 4 carbon atoms in each of the alkyl moieties. Among the preferred dialkylamino groups which can form the phosphorane of formula III above are included dimethylamino, diethylamino and diisopropylamino.

In accordance with another embodiment of this invention, the compounds of formula II above can be converted into the compounds of formula I-a above by reacting the compound of formula II above with the phosphone oxide of the formula IV above. In accordance with a preferred embodiment of this invention the phosphone oxide has the formula IV-a above. Generally, this reaction is carried out in the presence of an alkali metal base in an inert solvent. Any conventional alkali metal base can be utilized. Among the conventional alkali metal bases are included the alkali metal hydrides such as sodium hydride, potassium hydride; alkali metal lower alkoxides such as sodium methoxide, sodium ethoxide, etc.; and the alkali metal amide bases such as sodamide, potassium amide, sodium methylamide, potassium methylamide, as well as other alkali metal lower alkyl amides. In carrying out this reaction, any conventional inert organic solvent can be utilized, such as, benzene, toluene, N,N-dimethylformamide, tetrahydrofuran, dioxane, 1,2-dimethoxyethane. In carrying out this reaction, the temperature of from 0°C. to 30°C. should be utilized. The reaction of compounds of the formula II above with phosphine oxides of the formula IV or IV-a above to produce a compound of the formula I-a above can be carried out in the presence of a base such as an alkali metal alcoholate utilizing the corresponding alcohol as a solvent. In carrying out this reaction, any alkali metal alcoholate and any conventional alcohol, such as sodium ethylate and ethyl alcohol, can be utilized. However, when the phosphine oxide of formula IV-a above is utilized, it is preferable to avoid this procedure and carry out the reaction in the presence of a base such as alkali metal hydride or alkali metal lower alkyl amide.

According to a preferred embodiment of this invention, the compound of formula II above is reacted with a phosphine oxide of formula IV-a such as (methoxycarbonyl or ethoxycarbonylmethyl)-bis[2-chloro (or 2-methoxy)-phenoxy]-phosphine oxide in the presence of 2 moles of sodium hydride in absolute dioxane. In this preferred procedure, the excess sodium hydride is decomposed by the addition of absolute ethanol.

The phosphine oxides of formula IV above can be substituted by aryl, alkoxy or aryloxy groups. As with $R_1$, $R_2$ and $R_3$ in the phosphorane of formula III, the aryl groups denoted by $R_4$ and $R_5$ in the phosphine oxides of formula IV can be mononuclear or polynuclear aryl groups which may be substituted or unsubstituted. When the phosphine oxides of formula IV are substituted by alkoxy groups, it is generally preferred to utilize alkoxy groups containing from 1 to 4 carbon atoms such as methoxy, ethoxy and isopropoxy. Among the aryloxy groups, phenoxy groups which are substituted in the ortho-position by a halogen atom or a lower akoxy or dialkylamino are generally preferred.

In accordance with this invention, there has been found that where a phosphine oxide of the formula IV-a is utilized, the formation of the 2-cis isomer of the compound of the formula I-a is strongly favored.

In the compound of formula IV-a, Y represents an electron donating group or hydrogen. Any conventional electron donating group such as halogen, alkoxy or dilower alkylamine can be utilized as the substituent Y. Among the preferred phosphine oxides of formula IV-a are those compounds wherein Y, $Y_1$ and $Y_2$ are hydrogen and those compounds wherein $Y_1$ and $Y_2$ are hydrogen and Y represents a halogen atom, preferably chlorine, or an alkoxy group, preferably methoxy. When Y represents a dialkylamino group, the preferred dialkylaino group is dimethylamino.

Compounds of the formula VII above can be prepared by reacting compounds of the formula VI above with either a phosphorane of the formula III above or a phosphine oxide of the formula IV above. In carrying out this reaction the same condition described in connection with the reaction of compounds of the formula II above with the phosphorane of the formula III above and the phosphine oxide of the formula IV above to form the compound of the formula I-a above are utilized. When a phosphine oxide of the formula IV-a above is utilized in this reaction, the formation of the 2-cis isomer of the compound of the formula VII above is favored.

The new and unexpected results that are achieved by utilizing the phosphine oxide of formula IV-a can be seen from the fact that when 6-ethyl-10-methyl-dodecadien-(5-trans, 9-cis or trans)-one-(2) is reacted with (methoxycarbonyl-methyl)-triphenyl phosphorane or with (methoxycarbonyl-methyl)-diethoxyphosphine oxide, there is obtained a mixture consisting of about 80% by weight of 3,11-dimethyl-7-ethyl-tridecatriene-(2-trans, 6-trans, 10-trans)-oic-(1) acid methyl ester and about 20% by weight of 3,11-dimethyl-7-ethyl-tridecatriene-(2-cis, 6-trans, 10-trans)oic-(1) acid methyl ester.

On the other hand, when (ethoxycarbonyl-methyl)-bis[2chloro (or 2-methoxy)-phenoxy]-phosphine oxide is reacted with 6-ethyl-10-methyl-dodecadien(5-trans, 9-cis or trans)-one-2, there is obtained an isomeric mixture consisting of about 45% of the 2-cis and about 55% of the 2-trans in the mixture of 3,11-dimethyl-7-ethyl-tridecatrien-(2-cis/trans, 6-trans, 10-trans)-oic-(1)acid ethyl ester. As can be seen from this, the use of the phosphine oxide of formula IV-a greatly improves the yield of the 2-cis isomer that is obtained in the resulting isomeric mixture.

The phosphine oxide of formula IV is prepared by reacting a compound of the formula

X-CH₂-A' wherein X is halogen; A' is as above with a compound of the formula
P(OR₅)(OR₄)₂ wherein $R_4$ and $R_5$ are as above at a temperature of from 100°C. to 150°C. In this reaction a solvent need not be utilized. On the other hand, if desired, this reaction can be carried out in the presence of any conventional high boiling solvent such as decalin, tetralin, etc.

The compounds of formula VII above can be converted into the compounds of formula I-a above and the compounds of formula VI above can be converted into the compounds of formula II above by any conventional epoxidation technique. In accordance with this invention, the compounds of formula VI above and VII above can conveniently be epoxidized to the corresponding compounds of formula II above or I-a above by first treating either the compound of formula VI or the compound of formula VII above with N-bromosuccinimide in water to selectively and exclusively oxidize the terminal double bond giving rise to the corresponding bromohydrins. These bromohydrins are converted by the action of a base to the corresponding epoxides. The formation of the bromohydrins is carried out at a temperature of from 0°C. to 30°C. Any of the conventional bases such as the bases hereinbefore mentioned can be utilized in carrying out this conversion. Among the preferred bases which can be utilized in accordance with this invention are the alkali metal alcoholates such as sodium alcoholate. Generally, the conversion of bromohydrins to the corresponding epoxide is carried out in an alcoholic solvent such as methyl alcohol and ethyl alcohol.

Another means of converting the compound of the formula VI above or the compound of the formula VII above to the epoxide of the formula I-a above II above is by treating either the compound of the formula VI above or VII above with an organic peracid. Any conventional organic peracid can be utilized in this reaction. Among the conventional organic peracids which can be utilized are included peracetic acid, perbenzoic acid, 3-chloroperbenzoic acid and perphthalic acid. This reaction is usually carried out in an inert organic solvent. Any conventional inert organic solvent can be utilized. Among the inert organic solvents which can be utilized, the halogenated hydrocarbon solvents such as methylene chloride and chloroform are preferred. Generally, this reaction is carried out at a temperature of from about 0°C. to 30°C.

The compounds of formula I-a above wherein A' is a cyano group can be converted into the compounds of formula I above wherein A is a carboxy group by standard techniques such as hydrolysis with an inorganic acid or base. If desired, the carboxy compound of formula I can be converted into the corresponding amine by first treating the compound of formula I where A is a carboxyl group above with a halogenating agent such as phosphorus trichloride, phosphorus pentachloride, etc., to form the acid chloride. The standard techniques well-known in the art can be utilized for forming the acid chloride of the carboxylic acid of formula I above. The acid chloride of the carboxylic acid of formula I above can then be reacted with ammonia under standard and well-known conditions to form the compound of formula I wherein A is an aminocarbonyl group. Alternatively, the acid chloride of the carboxylic acid of formula I above can be reacted with an appropriate alkyl substituted amine such as a mono-lower alkyl amine or di-lower alkyl amine under standard and well-known conditions to form the compound of formula I wherein A is a lower alkyl-substituted amine.

If desired, the compound of formula I-a above wherein A' is an alkoxycarbonyl group can be converted to the compound of formula I wherein A is a carboxy group by any conventional technique of ester hydrolysis or saponification such as by treatment with an alkali, i.e., sodium hydroxide, potassium hydroxide, etc.

The compound of formula VI is prepared from a compound of the formula

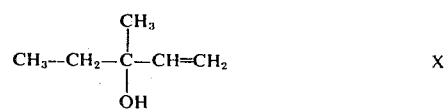

X by means of the following reaction scheme:

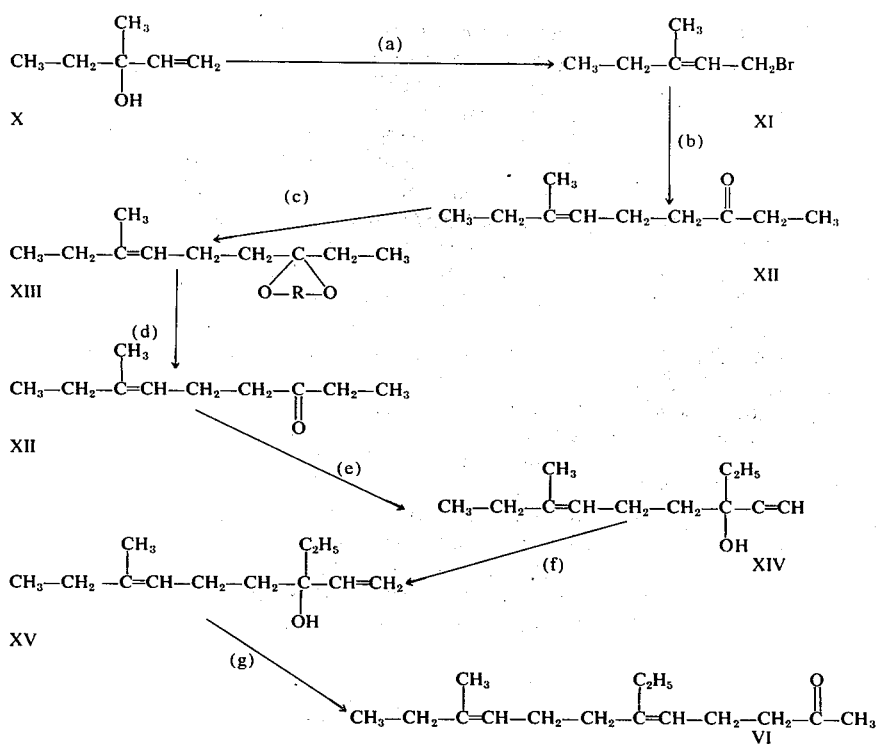

wherein R is lower alkylene such as an alkylene group containing from 2 to 6 carbon atoms, i.e., ethylene, propylene, isobutylene, etc.

The compound of formula X above is converted to the compound of formula XI above, via reaction step (a), by subjecting the compound of formula X above to bromination and allyl rearrangement. Any conventional method of bromination and allyl rearrangement can be utilized in carrying out the reaction of step (a). Generally, the bromination and allyl rearrangement can be carried out by treating the compound of formula X above with a brominating agent such as phosphorus tribromide in the presence of a base such as those hereinbefore mentioned. Among the preferred bases are the tertiary amines such as pyridine. In carrying out this reaction any conventional brominating agent and acid binding agent can be utilized. In carrying out this reaction, an inert organic solvent medium is generally utilized. Any conventional inert organic solvent such as petroleum ether can be utilized. Furthermore, this reaction is generally carried out in a temperature from about −15°C. to 30°C.

The compound of formula XI above is converted into the compound of formula XII above by reacting the compound of formula XI above with a propionyl acetic acid ester of the formula

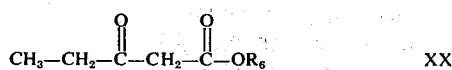

wherein $R_6$ is lower alkyl.

The reaction of step (b) is carried out by reacting the compound of the formula XX above with the compound of the formula XI above at temperatures of over 90°C., preferably up to about 120°C., with or without an inert organic solvent. In treating the compound of the formula XI above with a compound of the formula XX above a base is generally utilized as the catalyst. Any conventional base such as those hereinbefore mentioned can be utilized. Typical bases include sodium or potassium alkoxides such as sodium methoxide; tertiary amines such as pyridine; alkali metal hydroxides; etc. The reaction of step (b) can be carried out alone or in the presence of a conventional inert organic solvent.

The compound of formula XII above can be converted to the compound of formula XIII above, via reaction step (c), by reacting the compound of formula XII above with a lower alkylene glycol. Generally, this reaction is carried out in an inert organic solvent in the presence of an acid catalyst. Any conventional acid catalyst such as p-toluene sulfonic acid, boron trifluoride etherate, etc., can be utilized. Any conventional inert solvent such as the solvents hereinbefore mentioned can be utilized in this reaction. In this reaction, temperature and pressure are not critical and room temperature or elevated temperature can be utilized. Among the lower alkylene glycols which can be utilized in forming the compound of formula XIII above are included ethylene glycol, 2,3-butanediol, etc.

The reaction of step (a) produces the compound of formula XI which can exist in two geometric isomeric forms, i.e., the 2-trans form and the 2-cis form. These two isomeric forms are carried over by the reaction of step (b) to product the 2-one of formula XII which can exist in two geometric isomeric forms, i.e., the 6-trans or 6-cis form. The resulting isomeric mixture of formula XII above can be separated, if desired, by converting the compound of the formula XII above via reaction step (c) into the compound of the formula XIII above. The compound of the formula XII above is converted into a 74 percent by weight trans and a 26 percent by weight cis mixture of the compound of formula XIII. The compound of the formula XIII above can be easily separated into a trans and cis isomers by conventional chemical and/or physical methods. In separating the isomers which form the isomeric mixture of formula XIII above, it is generally preferred to utilize fractional distillation.

The compound of formula XIII can be converted back to the compound of formula XII above via reaction step (d) by treating the compound of the formula XIII with an acid hydrolyzing agent. Any conventional means of acid hydrolysis can be utilized to convert the compounds of formula XIII above back to the compounds of the formula XII above. Generally, it is preferred to utilize a dilute mineral or organic acid such as sulfuric acid, formic acid, or acetic acid in the presence of an inert organic solvent. Any conventional inert organic solvent can be utilized in carrying out this reaction. Generally, it is preferred to utilize a solvent which is miscible in water, such as a lower alkanol which may be methanol, ethanol, etc. or ketones, such as acetone. In carrying out this reaction, temperature and pressure are not critical and the hydrolysis reaction can be carried out at room temperature and atmospheric pressure or at elevated and reduced temperatures and pressures.

The compound of formula XII is converted to the compound of formula XIV by reaction step (e) by treating the compound of formula XII with an alkali metal acetylide in liquid ammonia. Generally, the alkali metal acetylide is obtained by bubbling acetylene gas into a liquid ammonia solution containing an alkali metal such as sodium or potassium. To this alkali metal acetylide dissolved in liquid ammonia, the compound of formula XII is added. The reaction of step (e) is carried out at a temperature below the reflux temperature of liquid ammonia. Generally, temperatures of from −60 to −30 are utilized.

The compound of formula XIV above is converted to the compound of formula XV above, as in step (e) by partial hydrogenation. Any conventional means of partial hydrogenation can be utilized. These methods include hydrogenating the compounds of the formula XIV above in the presence of a palladium catalyst poisoned with lead (see, e.g., H. Lindlar, Helv. Chim. Acta, 35, 1952).

The compound of formula XV can be converted to the compound of the formula VI above by reacting the compound of the formula XV with an enol ether of the formula

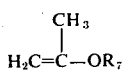

wherein $R_7$ is a lower alkyl.

The reaction of the step (g) is carried out in the presence of an acidic catalyst. Any conventional inorganic or organic acids can be utilized as a catalyst in this reaction. Among the suitable acids which can be utilized in accordance with this invention are included mineral acids such as phosphoric acid, sulfuric acid, etc.; organic acids, such as oxalic acid, trichloroacetic acid, p-toluene sulfonic acid, etc.; Lewis acids such as boron trichloride, boron trifluoride, zinc chloride, etc. Generally, this reaction is carried out at temperatures of above about 50°C., preferably at temperatures above about 100°C. Temperatures within the ranges of about 120°C. to about 200°C. are, in general, preferred. The reaction of step (g) can be carried out with, but also without, a solvent. As a solvent there can be used, for example, organic solvents, e.g., hydrocarbons such as hexane, cyclohexane, isooctane, benzene, toluene, petroleum ether, ligroin, etc. This reaction can be carried out at atmospheric or superatmospheric pressures.

Alternatively, the compound of formula XV above can be converted to the compound of formula VI above by means of the following reaction scheme:

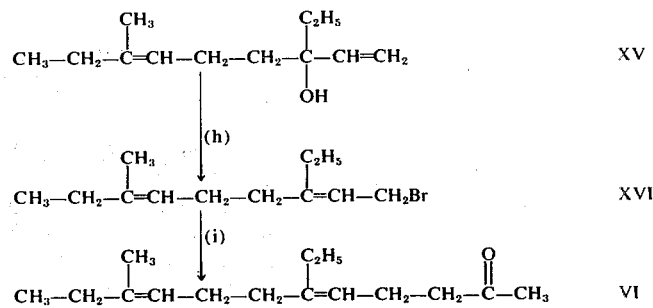

The reaction of step (h) is carried out by subjecting the compound of formula XV above to bromination and allyl rearrangement in the same manner as described in connection with step (a). In this manner, the compound of formula XV above is converted to the compound of formula XVI above.

The compound of formula XVI above is converted to the compound of formula VI above by reacting the compound of formula XVI, via reaction step (i) with an acetoacetic acid ester of the formula

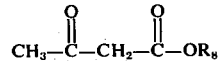

wherein $R_8$ is a lower alkyl.

The same conditions utilized in step (b) in connection with the conversion of compounds of the formula XI above to compounds of the formula XII above are utilized in carrying out reaction step (i).

The process of this invention can be utilized to produce the tridecadien of formula I above in the following geometric isomeric forms:
 2 cis, 6 trans, 10 trans; and
 2 cis, 6 trans, 10 cis.

Both of these two isomers as well as mixtures thereof possess the aforementioned beneficial pesticidal, endoparasitic and ectoparasitic properties.

On the other hand, the process of this invention can produce the compound of formula I above as a mixture of 2 cis, 6 trans, 10 trans; and
2 trans, 6 trans, 10 trans or as a mixture 2 cis, 6 trans, 10 cis; and
2 trans, 6 trans, 10 cis.

Alternatively, the tridecadien of formula I above can be produced as a mixture of the following four isomeric forms:

2 cis, 6 trans, 10 trans;
2 cis, 6 trans, 10 cis;
2 trans, 6 trans 10 cis; and
2 trans, 6 trans, 10 trans.

The various isomeric forms of the compound of formula I can be produced by separating the compound of formula XII above into its two geometric isomeric forms, i.e., 6 trans and 6 cis forms as in reaction step (c). From the 6 cis isomer of formula XII by the reaction scheme of this invention there is obtained the 5 cis/trans 9 cis isomeric mixture of the compound of formula VI above. This 5 cis/trans, 9 cis derivative of the formula VI above can be separated by conventional methods such as fractional distillation or vapor phase chromatography into its two geometric isomeric forms which are:

6-ethyl-10-methyl-dodecadien-(5-cis, 9-cis)-one-(2); and
6-ethyl-10-methyl-dodecadien-(5-trans, 9-cis)-one-(2).

Only the 6-ethyl-10-methyl-dodecadien-(5-trans, 9-cis)-one-(2) can be utilized in producing the compound of formula I in accordance with this process of this invention.

When the 6-trans isomer of the formula XII above is reacted in accordance with the aforementioned reaction schemes to produce a compound of the formula VI above, a mixture containing the following geometric isomers is formed:

6-ethyl-10-methyl-dodecadien-(5-cis, 9-trans)-one-(2); and
6-ethyl-10-methyl-dodecadien-(5-trans, 9-trans)-one-(2). These two geometric isomers can be separated by any conventional method such as fractional distillation or vapor phase chromatography. Of the above two geometric isomers of formula VI above only the 5-trans, 9-trans isomer can be utilized to produce the compound of the formula I above.

When the compound of formula VI above is epoxidized to form the compound of formula II above, no change in the isomeric structure of the compound of formula VI above occurs in this reaction. Therefore, the compound of formula II above has the same isomeric form as the compound of formula VI above from which it is formed.

However, when the aforementioned 5-trans, 9-trans isomer of formulae II or VI above are reacted with the phosphorane of formula III above or the phosphine oxide of formula IV above the compound of formulae I-a or VII is formed as a mixture of the 2 cis, 6 trans, 10 trans; and
2 trans, 6 trans, 10 trans isomers. When the 5-trans, 9-cis isomer of formulae II or VI above is reacted with the ether compounds of formulae III above or VI above, the compounds of formulae I-a or VII is formed as a mixture of the 2 cis, 6 trans, 10 cis; and
2 trans, 6 trans, 10 cis isomers. These mixtures can be separated, if desired, into their respective isomeric forms by conventional means such as fractional distillation or by adsorption on a material having selective affinity for the various isomers. In accordance with a preferred embodiment of this invention, each of the aforementioned isomeric mixtures of the compound of formula I-a above or VII above can be separated by dissolving the isomeric mixture in an organic solvent such as ethyl acetate, a mixture of hexane and diethyl ester, etc. and passing this solution over adsorptive material such as kieselgel which has selective affinity for the various isomers. The material adsorbs the isomeric mixture. The different isomers can be separated by elution utilizing the same solvent mixture.

The 2 cis/trans isomeric mixtures of formula VI can be, if desired, separated by the aforementioned means prior to epoxidation. Alternatively, the isomeric mixture of formula VII can be epoxidized to the form the isomeric mixture of formula I-a and then separated into its respective isomers by the aforementioned means.

In accordance with another embodiment of this invention, the isomeric mixture can, if desired, be separated during the step of treating with N-bromosuccinimide to form the corresponding epoxide.

The 10,11-bromohydrin of the compound of formula VII above which is formed when N-bromosuccinimide is reacted with the compound of formula VII above can be separated into the 2 cis and 2 trans forms by conventional methods. The preferred method for separating these two isomers is by the aforementioned adsorption on a material such as kieselgel which has a selective affinity for these two isomers. After these two isomers have been separated, they can be treated with a base in the aforementioned manner to form the respective 2 trans or 2 cis isomers of formula I-a above.

In accordance with another embodiment of this invention, the 5 trans, 9 trans isomer and the 5 trans, 9 cis isomer of formula VI can be combined and converted to the compound of formula I above by the aforementioned reaction scheme. In this manner, the compound of formula I is formed as a mixture of the following four isomers:

2 cis, 6 trans, 10,11 trans
2 cis, 6 trans, 10,11 cis
2 trans, 6 trans, 10,11 cis
2 trans, 6 trans, 10,11 trans. The following Examples are illustrative of the invention. In the Examples instead of exact boiling points, the boiling ranges measured in the distillation of the compounds in the bulb tube are given. The ether utilized in the foregoing Examples is diethyl ether.

EXAMPLE 1

Preparation of
trans-3,3-ethylenedioxy-7-methyl-nonene-(6) and
cis-3,3-ethylenedioxy-7-methyl-nonene-(6)

200 g. of 3-methyl-penten-(1)-ol-(3) are dissolved in 560 ml. of low-boiling petroleum ether and treated with 48 ml. of pure pyridine. To the resulting mixture, cooled to −6°C. to −7°C., there is added dropwise over the course of 2 hours a solution of 85 ml. of phosphorous tribromide in 500 ml. of petroleum ether. The resulting mixture is subsequently stirred at room temperature for an additional 2 hours and, after the addition of 600 ml. of low-boiling petroleum ether, poured into 2000 ml. of ice-water and stirred at +3°C. for 0.5 hour. The petroleum ether phase is then separated off, successively washed twice with 1000 ml. each of a saturated aqueous sodium bicarbonate solution and of a saturated aqueous sodium chloride solution, dried over sodium sulphate and evaporated under reduced pressure at 30°C. bath-temperature. The residual oily pale yellow-colored cis/trans 1-bromo-3-methyl-pentene-(2) is used without further purification.

48 g. of sodium are dissolved little by little in 1200 ml. of absolute ethanol. 290 g. of propionyl-acetic acid ethyl ester are added dropwise to the resulting solution at 40°–45°C. over a period of 0.25 hour. The resulting mixture is cooled to 0°C. and treated dropwise over the course of 3 hours at 3°–5°C. with 335 g. of cis/trans 1-bromo-3-methyl-pentene-(2). The resulting suspension is heated under reflux conditions for about 2 hours, then treated at boiling heat for a period of 2 hours with 3000 ml. of a 10 percent by weight aqueous sodium hydroxide solution and stirred under reflux conditions for a further 2 hours. The mixture is subsequently cooled to room temperature and extracted with 3000 ml. of low-boiling petroleum ether. The extract is washed with two 1,000 ml. portions of a saturated aqueous sodium chloride solution, dried over sodium sulphate and evaporated. The residual cis/trans 7-methyl-nonen-(6)-one-(3) is purified by distillation (boiling point = 86°–89°C./11 mmHg).

100 g. of cis/trans 7-methyl-nonen-(6)-one-(3) are introduced into 500 ml. of ethyleneglycol and 250 ml. of absolute ether and treated dropwise with intensive stirring over a period of 10 minutes while cooling at 20°–24°C. with a solution of 150 ml. of boron trifluoride etherate in 250 ml. of absolute ether. The resulting mixture is stirred at 20°C. for 14 hours, diluted with 1000 ml. of ether, poured into 4000 ml. of a saturated aqueous sodium bicarbonate solution, successively washed with 1500 ml. of a saturated aqueous sodium bicarbonate solution and with 500 ml. of water and subsequently extracted with two 1000 ml. portions of ether. The extracts are combined, dried over potassium carbonate and evaporated. The residual 3,3-ethylenedioxy-7-methyl-nonene-(6) (boiling point = 103°–113°C./12 mmHg) consisting of about 26 percent cis and 74 percent trans isomers is separated by distillation in a Podbielniak-Hell-grid column to separately yield trans 3,3-ethylenedioxy-7-methyl-nonene-(6) and the cis 3,3-ethylenedioxy-7-methyl-nonene-(6).

EXAMPLE 2

Preparation of trans-7-methyl-nonen-(6)-one-(3)

169 g. of trans 3,3-ethylenedioxy-7-methyl-nonene-(6) are dissolved in 950 ml. of dioxan and treated dropwise with 1350 ml. of 3-N sulphuric acid. The resulting mixture is stirred at 39°C. for 15 hours, then poured into 4000 ml. of ice-water and extracted with three 2000 ml. portions of hexane. Th extracts are washed with two 2000 ml. portions of a saturated sodium chloride solution, dried over sodium sulphate and evaporated to give trans 7-methyl-nonen-(6)-one-(3) (boiling point = 90°–92°C./12 mmHg) as the residue.

EXAMPLE 3

Preparation of 3-ethyl-7-methyl-nonadien-(1,6-trans)-ol-(3)

17.3 g. of sodium and 2.9 g. of potassium are cautiously introduced in small pieces with stirring over a period of 0.5 hour into 450 ml. of liquid ammonia cooled to about −40°C. Acetylene is led into the resulting blue-colored solution at −40°C. until the color of the solution changes to white. With acetylene still being led in, the solution is then treated dropwise at −42°C. to −45°C. over a period of 2 hours with 111.6 g. of trans 7-methyl-nonen-(6)-one-(3) and subsequently over the course of 1 hour with 45 g. of ammonium chloride. The acetylene stream is interrupted and the resulting mixture is stirred for 12 hours without cooling in order to substantially evaporate off the ammonia. The mixture is then treated with 400 ml. of ether, carefully concentrated, cooled to 0°C., treated dropwise with stirring over a period of 0.5 hour with 400 ml. of water and further stirred for 0.5 hour. The mixture is subsequently extracted with three 400 ml. portions of ether. The extracts are combined, washed successively with two 400 ml. portions of 0.5-N sulphuric acid and two 400 ml. portions of a saturated aqueous sodium chloride solution, dried over sodium sulphate and evaporated to give trans 3-ethyl-7-methyl-nonen-(6)-yn-(1)-ol-(3) (boiling point = 110°-113°C./12 mmHg) as the residue.

127.2 g. of trans 3-ethyl-7-methyl-nonen-(6)-yn-(1)-ol-(3) are dissolved in 650 ml. of petroleum ether (boiling range = 80° to 103°C.) and to the solution are added 12.7 g. of a partially inactivated lead/palladium catalyst and 12.7 ml. of quinoline, then the mixture is hydrogenated. The supply of hydrogen is interrupted after the uptake of the theoretical amount of hydrogen. The catalyst is filtered off and the filtrate is extracted with 110 ml. of 1-N sulphuric acid. The petroleum ether layer is washed with two 100 ml. portions of a saturated aqueous sodium chloride solution, dried over sodium sulphate and evaporated to give 3-ethyl-7-methyl-nonadien-(1,6 trans)-ol-(3) (boiling point = 110°-113°C./13 mmHg) as the residue.

EXAMPLE 4

Preparation of 6-ethyl-10-methyl-dodecadien-(5 trans, 9 trans) one-(2)

121.7 g. of 3-ethyl-7-methyl-nonadien-(1,6 trans)-ol-(3), 0.4 g. of phosphoric acid and 98.5 g. of isopropenyl methyl ether are heated at 180°C. in an argon atmosphere in a closed system (pressure = 2 atmospheres gauge) for 1.25 hours. The resulting mixture is cooled to room temperature and, after the addition of 10 ml. of triethyl amine, evaporated under reduced pressure. The residual 6-ethyl-10-methyl-dodecadien-(5 cis/-trans, 9 trans)-one-(2), consisting of about 52 percent of the 5 cis and 48 percent of the 5 trans isomers, is separated by distillation in a Podbelniak-Hell-grid column. The 6-ethyl-10-methyl-dodecadien-(5 trans, 9 trans)-one-(2) obtained boils at 80°-83.5°C./0.5-0.8 mmHg.

EXAMPLE 5

Preparation of 6-ethyl-10-methyl-dodecadien-(5 trans, 9 trans)-one-(2)

45 ml. of low-boiling petroleum ether and 3.8 ml. of absolute pyridine are added to 28.6 g. of 3-ethyl-7-methyl-nonadien-(1,6 trans)-ol-(3) prepared in Example 3 and the mixture is cooled to −7°C. and treated over a period of 1.5 hours with a solution of 6 ml. of phosphorus tribromide in 35 ml. of lowboiling petroleum ether. The mixture is subsequently stirred at room temperature for 2 hours, diluted with 100 ml. of low-boiling petroleum ether, poured into ice-water and stirred for 0.5 hour. The petroleum ether phase is separated, successively washed with a saturated aqueous sodium bicarbonate solution and a saturated aqueous sodium chloride solution, dried over sodium sulphate and evaporated under reduced pressure at 30°C. to give 1-bromo-3-ethyl-7-methyl-nonadiene-(2 cis/trans, 6 trans) as the residue.

34.7 g. of 1-bromo-3-ethyl-7-methyl-nonadiene-(2 cis/trans, 6 trans) are added dropwise at 0°C. over a period of 2 hours to a solution of 3.22 g. of sodium in 84 ml. of absolute ethanol. The resulting mixture, gradually rising to room temperature, is allowed to stand for 12 hours. It is subsequently heated under reflux conditions for a further 2 hours, then treated at 80°C. over a period of 1 hour with 210 ml. of 10 percent by weight sodium hydroxide solution and again stirred under reflux conditions for 3 hours. The mixture is subsequently cooled, poured into ice-water and exhaustively extracted with hexane. The combined hexane extracts are washed with a saturated aqueous sodium chloride solution, dried over sodium sulphate and evaporated. The residual 6-ethyl-10-methyl-dodecadien-(5 cis/-trans, 9 trans)-one-(2), consisting of about 58 percent cis and 42 percent trans isomers, is purified by distillation. The pure isomer mixture boils at 68°–71°C./0.03 mmHg.

The foregoing isomer mixture can be separated by fractional distillation in a Podbielniak-Hell-grid column into gas-chromatographically 100 percent pure 6-ethyl-10-methyl-dodecadien-(5 cis, 9 trans)-one-(2) (boiling point = 81°-82°C./0.8 mmHg) and 6-ethyl-10-methyl-dodecadien-(5 trans, 9 trans)-one-(2) (boiling point = 80°-83.5°C./0.5-0.8 mmHg).

Example 6

Preparation of 7-ethyl-3,11-dimethyl tridecatrien-(2 cis, 6 trans, 10 trans)oic-(1)-acid methyl ester and the corresponding 2 trans, 6 trans, 10 trans isomer 16.1 g. of 6-ethyl-10-methyl-dodecadien-(5 trans, 9 trans)-one-(2) and 15.2 g. of (methoxycarbonyl-methyl)-diethoxy-phosphine oxide are dissolved in 165 ml. of N,N-dimethyl-formamide, cooled to 0°-5°C. and treated dropwise with a solution of 1.66 g. of sodium in 17.5 ml. of absolute methanol. The resulting mixture is stirred at 40°C. for 4 hours, then cooled to room temperature, poured into 1000 ml. of saturated aqueous sodium chloride solution and extracted with five 200 ml. portions of petroleum ether. The combined extracts are washed with a saturated aqueous sodium chloride solution, dried over sodium sulphate and evaporated. The residual isomer mixture, consisting of about 20 percent by weight 7-ethyl-3,11-dimethyl-tridecatrien-(2 cis, 6 trans, 10 trans)oic-(1) acid methyl ester and about 80 percent by weight of the corresponding 2 trans compound, can be separated by repeated adsorption on kieselgel and elution with a solvent mixture containing 92.5 parts by volume of hexane and 7.5 parts by volume of ethyl acetate to give 7-ethyl-3,11-dimethyltridecatrien-(2 cis, 6 trans, 10 trans)oic-(1) acid methyl ester boiling at 102°-104°C./0.2 mmHg and 7-ethyl-3,11-dimethyltridecatrien-(2 trans, 6 trans, 10 trans)oic-(1) acid methyl ester boiling at 104°-108°C./0.02 mmHg.

Example 7

Preparation of racemic 10,11-epoxy-7-ethyl-3,11-dimethyl-10,11-trans tridecadien-(2 cis, 6 trans)oic-(1)-acid methyl ester 3 g. of 7-ethyl-3,11-dimethyl-tridecatrien-(2 cis, 6 trans, 10 trans)oic-(1) acid methyl ester are dissolved in 30 ml. of methylene chloride, cooled to 0°-5°C. and treated little by little with 2.3 g. of 79 percent by weight of 3-chloro-perbenzoic acid. The resulting mixture is stirred at 0°-5°C. for 5 hours and subsequently poured into 20 ml. of ice-cold aqueous 1-N sodium hydroxide solution. The alkaline aqueous phase is separated off and extracted with three 45 ml. portions of methylene chloride. The combined extracts are washed with an ice-cold aqueous 1-N sodium hydroxide solution and subsequently with a saturated aqueous sodium chloride solution, dried over sodium sulphate and evaporated. The residual crude racemic 10,11-epoxy-7-ethyl-3,11-dimethyl-10,11-trans-tridecadien-(2 cis, 6 trans)oic-(1) acid methyl ester can be purified by adsorption on kieselgel and elution with 90 parts by volume of hexane and 10 parts by volume of ether mixture. The pure compound boils at 122°-125°C./0.03 mmHg.

EXAMPLE 8

Preparation of racemic 9,10-epoxy-6-ethyl-10-methyl-9,10-transdodecen-(5 trans)-one-2

20 g. of 6-ethyl-10-methyl-dodecadien-(5 trans, 9 trans)one-(2) are dissolved in 200 ml. of methylene chloride, cooled to 0°-5°C. and treated little by little with 23.6 g. of 79 percent by weight of 3-chloro-perbenzoic acid. The resulting mixture is allowed to stand in the cold for 16 hours and is subsequently poured into 150 ml. of ice-cold aqueous 1-N sodium hydroxide solution. The alkaline aqueous phase is separated off and extracted with three 150 ml. portions of methylene chloride. The combined extracts are washed with an ice-cold aqueous 1-N sodium hydroxide solution and subsequently with a saturated aqueous sodium chloride solution, dried over sodium sulphate and evaporated. The residual crude racemic 9,10-epoxy-6-ethyl-10-methyl-9,10-trans-dodecen-(5 trans) 2)-can be purified by adsorption on kieselgel and elution with hexane/ether (90:10 parts by volume). The pure compound boils at 110°-112°C./0.001 mmHg.

EXAMPLE 9

Cis 3,3-ethylenedioxy-7-methyl-nonene-(6) is converted into 9,10-epoxy-6-ethyl-10-methyl-9,10-cis-dodecen-(5 trans)-one-2 by the following procedure:

Cis 3,3-ethylenedioxy-7-methyl-nonene-(6) is treated with sulfuric acid by the procedure of Example 2 to produce cis 7-methyl-nonen-6-one-(3). The cis 7-methyl-nonene-6-one-(3) is treated with acetylene by the procedure of Example 3 to give cis-3-ethyl-7-methyl-nonen-(6)-yn-(1)-ol-(3) and then hydrogenated by the procedure of Example 3 to give 3-ethyl-7-methylnonadien-(1,6-cis) 3).

The 3-ethyl-7-methyl-nonadien-(1,6-cis)-ol-(3) is then treated with isopropenyl methyl ether in the manner of Example 4 to produce 6-ethyl-10-methyl-dodecadien-(5 cis/trans, 9 cis)-one-(2) which is then separated in the manner set forth in Example 4 to produce 6-ethyl-10-methyl-dodecadien-(5 trans, 9 cis)-one-(2).

The 6-ethyl-10-methyl-dodecadien-(5 trans, 9 cis)-one-(2) is epoxidized and purified by the procedure given in Example 8 to yield the racemic 9,10-epoxy-6-ethyl-10-methyl-9,10-cis-dodecen-(5 trans)-one-(2).

Example 10

Preparation of 10,11-epoxy-7-ethyl-3,11-dimethyl-10,11-transtridecadien-(2 cis, 6 trans)-oic-(1)-methyl ester 11.2 g. of racemic 9,10-epoxy-6-ethyl-10-methyl-9,10-transdodecen-(5 trans)-one-(2) and 11.6 g. of (methoxycarbonylmethyl)-diethoxy-phosphine oxide are dissolved in 110 ml. of N,N-dimethyl-formamide, cooled to 0°-5°C. and treated dropwise with a solution of 1.27 g. of sodium in 13.4 ml. of absolute methanol. The resulting mixture is stirred at 40°-45°C. for 8 hours, then cooled to room temperature, poured into 150 ml. of water and extracted with three 150 ml. portions of methylene chloride. The combined extracts are washed with a saturated aqueous sodium chloride solution, dried over sodium sulphate and evaporated. The residual isomer mixture, consisting of about 21 percent of racemic 10,11-epoxy-7-ethyl-3,11-dimethyl-10,11-trans-tridecadien-(2 cis, 6 trans)-oic-(1) acid methyl ester and about 79 percent of the corresponding 2-trans compound can be separated by repeated adsorption on kieselgel and elution with hexane/ether (90:10 parts by volume). Racemic 10,11-epoxy-7-ethyl-3,11-dimethyl-10,11-trans-tridecadien-(2 cis, 6 trans)-oic-(1) acid methyl ester boils at 123°-128°C./0.02 mmHg and racemic 10,11-epoxy-7-ethyl-3,11-dimethyl-10,11-trans-tridecadien-(2 trans, 6 trans)-oic-(1) acid methyl ester boils at 125°-128°C./0.02 mmHg.

EXAMPLE 11

By utilizing the procedure of Example 10, racemic 9,10-epoxy-6-ethyl-10-methyl-9,10-cis-dodecen-(5 trans)-one-(2) is converted to racemic 10,11-epoxy-7-ethyl-3,11-dimethyl-10,11-cis-tridecadien-(2 cis, 6 trans)-oic-(1) acid methyl ester.

EXAMPLE 12

Preparation of racemic 10,11-epoxy-7-ethyl-3,11-dimethyl-10,11-trans-tridecadien-(2 cis, 6 trans) 1) acid 1.5 g. of racemic 10,11-epoxy-7-ethyl-3,11-dimethyl-10,11-trans-tridecadien-(2 cis, 6 trans)-oic-(1) acid methyl ester are introduced into 50 ml. of a 0.5-N aqueous ethyl alcohol solution of sodium hydroxide. This solution consists of 1 part by volume water and 1 part by volume ethyl alcohol. The resulting mixture is stirred at 40°C. for 48 hours, then cooled to room temperature, diluted with 150 ml. of water, extracted with ether to remove unsaponified ester, then carefully acidified with 0.5-N aqueous hydrochloric acid while cooling with ice and exhaustively extracted with ether. The combined extracts are washed neutral with a saturated aqueous sodium chloride solution, dried over sodium sulphate and evaporated under reduced pressure at room temperature. The residue is dissolved in methanol. The resulting solution is shaken with 300 mg. of active carbon, briefly heated to 40°C., then filtered and evaporated under reduced pressure at room temperature. The residual racemic 10,11-epoxy-7-ethyl-3,11-dimethyl-10,11-trans-tridecadien-(2 cis, 6 trans)oic-(1) acid is dried in high vacuum.

EXAMPLE 13

Racemic 10,11-epoxy-7-ethyl-3,11-dimethyl-10,11-cis-tridecadien-(2 cis, 6 trans)-oic-(1) acid methyl ester is converted into racemic 10,11-epoxy-7-ethyl-3,11-dimethyl-10,11-cis-tridecadien-(2 cis, 6 trans)-oic-(1) acid by means of the process given in Example 12.

EXAMPLE 14

Preparation of 7-ethyl-3,11-dimethyl-10,11-trans-tridecatrien(2-cis/-trans, 6 trans)-oic-(1) acid diethylamide 4.8 g. of sodium hydride (as a 50 percent suspension in mineral oil) are twice suspended in 25 ml. hexane in order to remove the mineral oil. The hexane solution is decanted off. The residual sodium hydride is suspended in 50 ml. of absolute dioxan and the solution is cooled to 10°-12°C., treated dropwise with 12.6 g. (diethyl-amino carbonyl-methyl)-diethoxy-phosphine oxide and stirred at room temperature for 1.5 hours. The mixture is subsequently again cooled to 10°-12°C. and, after the addition of 11.1 g. 6-ethyl-10-methyl-dodecadien-(5-trans, 9-trans)-one-(2), stirred at room temperature for 20 hours. The mixture is thereafter treated, with ice-cooling, with 8 ml. of absolute ethanol in order to decompose the excess sodium hydride, then poured into a saturated aqueous sodium chloride solution and exhaustively extracted with ether. The combined ether extracts are washed neutral, dried and evaporated.

The residual 7-ethyl-3,11-dimethyl-10,11-trans-tridecatrien(2-cis/trans, 6-trans)-oic-(1) acid diethylamide is purified by distillation (12.3 g. boiling point = 129°-130°C./0.001 mmHg).

EXAMPLE 15

Preparation of 7-ethyl-3,11-dimethyl-tridecatrien-(2-cis/trans, 6-trans, 10-cis)-oic-(1) acid ethyl ester 1.64 g. of sodium hydride (as a 50 percent suspension in mineral oil) are twice suspended in 20 ml. portions of hexane in order to remove the mineral oil. The hexane solution is decanted off. The residual sodium hydride is suspended in 20 ml. of absolute dioxan and the solution is cooled to 0°-5°C., treated dropwise at this temperature with 6.65 g. of (ethoxycarbonyl-methyl)-bis(2-chloro-phenoxy)-phosphine oxide and stirred at room temperature for 0.5 hour. The mixture is subsequently again cooled to 0°-5°C. and, after the addition of 3.8 g. of 6-ethyl-10-methyl-dodecadien-(5 trans, 9 cis)-one-(2), stirred at room temperature for 16 hours. The mixture is thereafter treated, with ice-cooling, with 10 ml. of absolute ethanol in order to decompose the excess sodium hydride, then poured into 500 ml. of a saturated aqueous sodium chloride solution and exhaustively extracted with hexane. The combined hexane extracts are washed with a saturated aqueous sodium chloride solution, dried over sodium sulphate and evaporated. The residual 7-ethyl-3,11-dimethyltridecatrien-(2 cis/trans, 6 trans, 10 cis)-oic-(1) acid ethyl ester is purified by adsorption on kieselgel and consists of about 45 percent by weight cis and 55 percent by weight trans isomers; boiling point = 108°–115°C./0.02 mmHg.

EXAMPLE 16

This example is directed to the epoxidation of 7-ethyl-3,11-dimethyl-tridecatrien-(2-cis/trans, 6 trans, 10 trans)-oic-(1) acid ethyl ester.

To a homogeneous solution of 4.75 g. of 7-ethyl-3,11-dimethyl-tridecatrien-(2-cis/trans, 6-trans, 10-trans)-oic-(1) acid ethyl ester, 8 ml. water and 50 ml. tetrahydrofuran are added portionwise at a temperature of 0°–3°C. 3 g. of N-bromosuccinimide the mixture is stirred at this temperature for 6 hours, then poured into 500 ml. of a saturated aqueous sodium chloride solution and extracted with hexane. The combined hexane extracts are washed with a saturated aqueous sodium chloride solution, dried over sodium sulphate and evaporated. The residual 10-bromo-11-hydroxy-7-ethyl-3,11-dimethyl-10,11-trans-tridecadien-(2-cis/-trans, 6-trans)-oic-(1) acid ethyl ester is purified by adsorption on kieselgel and elution with hexane/ethyl acetate (85:15 parts by volume). If necessary, the 2-cis/trans-mixture of the above bromohydrin can be separated with the same solvent system on kieselgel into the following isomers:

10-bromo-11-hydroxy-7-ethyl-3,11-dimethyl-10,11-trans-tridecadien-(2-cis, 6-trans)-oic-(1) acid ethyl ester; and 10-bromo-11-hydroxy-7-ethyl-3,11-dimethyl-10,11-trans-tridecadien-(2-trans, 6-trans)-oic-(1) acid ethyl ester.

The bromohydrins of this type decompose on distillation.

4.3 g. of 10-bromo-11-hydroxy-7-ethyl-3,11-dimethyl-10,11-trans-tridecadien-(2-cis/trans, 6-trans)-oic-(1) acid ethyl ester in 5.5 ml. of absolute ethanol is treated at 0°C. with a solution of 0.253 g. of sodium, dissolved in 5.5 ml. of absolute ethanol, stirred for 1 hour at room temperature, poured into 250 ml. of a saturated aqueous sodium chloride solution and exhaustively extracted with hexane. The combined hexane extracts are washed with a saturated aqueous sodium chloride solution, dried over sodium sulphate and evaporated. The residual 10,11-epoxy-7-ethyl-3,11-dimethyl-10,11-trans-tridecadien(2-cis/trans, 6-trans)-oic-(1) acid ethyl ester is purified by distillation (boiling point = 120°C./0.001 mmHg).

EXAMPLE 17

7-Ethyl-3,11-dimethyl-tridecatrien-(2-cis/trans, 6-trans, 10-cis)oic-(1) acid ethyl ester is epoxidized by the process described in Example 16 to 10,11-epoxy-7-ethyl-3,11-dimethyl-10,11-cis-tridecadien-(2-cis/trans, 6-trans)-oic-(1) acid ethyl ester.

EXAMPLE 18

7-Ethyl-3,11-dimethyl-10,11-trans-tridecatrien-(2-cis/trans, 6-trans)-oic-(1) acid diethyl amide is epoxidized by the process of Example 16 to 10,11-epoxy-7-ethyl-3,11-dimethyl-10,11-transtridecadien-(2-cis/-trans, 6-trans)-oic-(1) acid diethyl amide.

EXAMPLE 19

6-Ethyl-10-methyl-dodecadien-(5-trans, 9-trans)-one-(2) is converted to 7-ethyl-3,11-dimethyl-trideca-trien-(2-cis/trans, 6-trans, 10 trans)-one-(1)-acid ethyl ester by the process disclosed in Example 15.

Examples 20 to 25 are directed to the use of the novel epoxides of this invention as pest control agents:

EXAMPLE 20

50 g. of bran are impregnated with an acetone solution of one of the epoxides listed hereinafter and used as the feed of 150 last-stage larvae of Tenebrio molitor. In the following list, the numbers in parentheses following the name of the individual epoxide indicate the ratio of the number of beetles hatching from the pupated larvae after 42 days to the total number of larvae:

racemic 10,11-epoxy-7-ethyl-3,11-dimethyl-10,11-transtridecadien-(2 cis, 6 trans)-oic-(1) acid methyl ester (0/150);

racemic 10,11-epoxy-7-ethyl-3,11-dimethyl-10,11-transtridecadien-(2 cis, 6 trans)-oic-(1) acid (14/150);

racemic 10,11-epoxy-7-ethyl-3,11-dimethyl-10,11-cistridecadien-(2 cis, 6 trans)-oic-1) acid methyl ester (8/150);

racemic 10,11-epoxy-7-ethyl-3,11-dimethyl-10,11-cistridecadien-(2 cis, 6 trans)-oic-(1) acid (6/150);

controls (67/150).

EXAMPLE 21

Woollen discs (diameter = 30 mm) are soaked with an acetone solution of racemic 10,11-epoxy-7-ethyl-3,11-dimethyl-10,11-trans-tridecadien-(2 cis, 6 trans)-oic-(1) acid methyl ester in acetone and 10 larvae of the clothes moth (Tineola biselliella) are placed on each disc. Larvae placed on untreated woollen discs develop into caterpillars which pupate undisturbed and moths are released from resulting pupae. The larvae placed on treated woollen discs are distributed in caterpillarformation and pupation. The number of moths which are released from the pupae in each of the treated and untreated discs appears in the following table:

| mg of active substance per woollen disc | number of living caterpillars | number of pupae | number of moths | damage in % |
|---|---|---|---|---|
| 0.0 | 8 | 14 | 4 | 60 |
| 5.0 | 9 | 32 | 0 | 9 |
| 10.0 | 5 | 121 | 0 | 7 |

EXAMPLE 22

Corrugated cardboard strips (20 × 50 mm) are soaked with an acetone solution of racemic 10,11-epoxy-7-ethyl-3,11-dimethyl-10,11-trans-tridecadien-(2 cis, 6 trans)-oic-(1) acid methyl ester and subjected to ready-to-pupate larvae of the codling moth (Carpocapsa pomonella). The larvae placed on the untreated cardboard crawl into the cavities of the corrugated cardboard, cocoon themselves and, after 14 days, release the moth. The larvae put on to treated cardboard are disturbed in caterpillarformation and pupation. The results of this treatment is shown in the following table:

| mg of active substance per corrugated cardboard | Number of caterpillars and pupae | | Number of moths | |
|---|---|---|---|---|
| | normal | dead | normal | deformed |
| 0.0 | — | — | 15 | 0 |

| mg of active substance per corrugated cardboard | -continued Number of caterpillars and pupae | | Number of moths | |
|---|---|---|---|---|
| 10.0 | 0 | 2 | 0 | 2 |
| 30.0 | 0 | 1 | 0 | 0 |

EXAMPLE 23

Ready-to-pupate larvae of the Colorado beetle (*Leptinotarsa decemlineata*) are sprayed with a 0.1% solution of racemic 10,11-epoxy-7-ethyl-3,11-dimethyl-10,11-trans-tridecadien-(2 cis, 6 trans)-oic-(1) acid methyl ester in acetone and placed on potato plants. A pupation delay of 2 days is found in comparison with the control group.

EXAMPLE 24

100 g. portions of wheat grain are soaked with a solution of racemic 10,11-epoxy-7-ethyl-3,11-dimethyl-10,11-trans-tridecadien-(2 cis, 6 trans)-oic-(1) acid methyl ester in acetone, dried and infected with 100 grain weevils (*Calandra granaria*). The weevils are sieved off after 14 days and observed for 6 weeks. Weevils fed with untreated grain reproduce normally. The weevils fed with the treated grain exhibit marked disturbances of development. The results of this experiment is given in the following table:

| mg. of active substance per 1 g. of wheat | Reproduction factor |
|---|---|
| 0.0 | 5.3 |
| 0.05 | 2.5 |
| 0.50 | 0.05 |

We claim:

1. A process for producing an isomeric mixture containing a 2-cis, 6-trans-3,11-dimethyl-7-ethyl-trideca derivative of the formula:

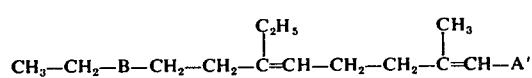

wherein B is 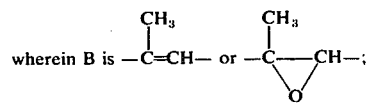

A' is cyano, lower alkoxy carbonyl, amino carbonyl or lower alkyl substituted amino carbonyl and its corresponding 2-trans, 6-trans geometric isomer comprising reacting a compound selected from the group consisting of a 5-trans, 9-cis-2-one of the formula:

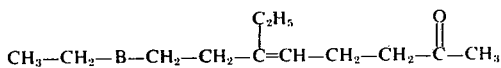

wherein B is as above
its corresponding 5-trans, 9-trans geometric isomer and mixtures with a phosphine oxide of the formula:

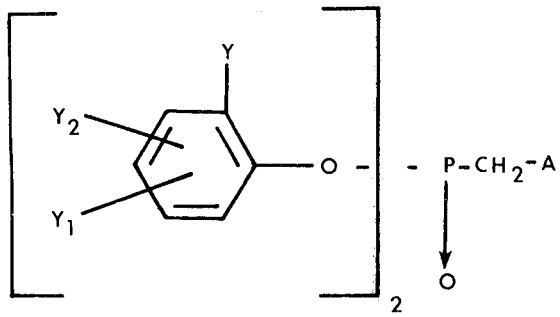

wherein A' is as above, Z is lower alkyl, Y is hydrogen, halogen, lower alkoxy or lower dialkyl-amino and $Y_1$ and $Y_2$ are selected from the group consisting of hydrogen, halogen, lower alkoxy and nitro wherein said lower alkyl and lower alkoxy groups each have from 1 to 6 carbon atoms to form said isomeric mixture.

2. The process of claim 1 comprising the additional step of separating said isomeric mixture into the 2-cis, 6-trans and 2-trans, 6-trans- isomers.

3. The process of claim 1 wherein A' is lower alkoxy carbonyl comprising the additional step of saponifying said isomeric mixture to form a carboxy compound of the formula:

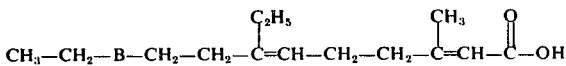

wherein B is as above.

4. The process of claim 1 wherein said phosphine oxide is (methoxycarbonyl-methyl)-bis(2-chlorophenoxy)-phosphine oxide.

5. The process of claim 1 wherein said phosphine oxide is (ethoxycarbonyl-methyl)-bis(2-chlorophenoxy)-phosphine oxide.

* * * * *